(12) United States Patent
Masumura

(10) Patent No.: US 8,326,567 B2
(45) Date of Patent: Dec. 4, 2012

(54) MEASUREMENT APPARATUS

(75) Inventor: Takahiro Masumura, Tucson, AZ (US)

(73) Assignee: Canon Kabushiki Kaisha, Tokyo (JP)

( * ) Notice: Subject to any disclaimer, the term of this patent is extended or adjusted under 35 U.S.C. 154(b) by 365 days.

(21) Appl. No.: 12/556,670

(22) Filed: Sep. 10, 2009

(65) Prior Publication Data

US 2010/0070233 A1 Mar. 18, 2010

(30) Foreign Application Priority Data

Sep. 17, 2008 (JP) ................. 2008-237253

(51) Int. Cl.
*G06M 7/02* (2006.01)
*G06M 7/08* (2006.01)
*G01N 30/16* (2006.01)
*G01N 30/18* (2006.01)

(52) U.S. Cl. ......... 702/127; 702/128; 702/138; 702/139

(58) Field of Classification Search .................... 702/19, 702/103, 104, 127, 182, 183, 189; 356/73; 359/330

See application file for complete search history.

(56) References Cited

U.S. PATENT DOCUMENTS

| | | | | |
|---|---|---|---|---|
| 6,738,653 | B1 | 5/2004 | Sfez et al. ..................... | 600/322 |
| 7,864,307 | B2 * | 1/2011 | Fukutani et al. ................. | 356/73 |
| 7,916,283 | B2 * | 3/2011 | Fukutani et al. ................. | 356/73 |
| 2005/0085725 | A1 | 4/2005 | Nagar et al. .................. | 600/437 |
| 2009/0066949 | A1 | 3/2009 | Masumura .................... | 356/326 |
| 2009/0069653 | A1 | 3/2009 | Yoshida et al. ............... | 600/323 |
| 2009/0069674 | A1 * | 3/2009 | Masumura et al. ........... | 600/425 |
| 2009/0069685 | A1 | 3/2009 | Nishihara et al. ............. | 600/443 |
| 2010/0226003 | A1 * | 9/2010 | Lefebvre et al. .............. | 359/330 |

FOREIGN PATENT DOCUMENTS

WO 02/08740 A2 1/2002

OTHER PUBLICATIONS

V Tuchin, *Handbook of Optical Biomedical Diagnostics*, pp. 585-646.
R Esenaliev et al., Sensitivity of Laser Opto-Acoustic Imaging in Detection of Small Deeply Embedded Tumors, *IEEE Journal of Selected Topics in Quantum Electronics*, vol. 5, No. 4 (1999).
M Xu et al., "Photoacoustic Imaging in Biomedicine", *Review of Scientific Instruments* 77, 041101 (2006).
M Oraevsky et al., "Measurement of Tissue Optical Properties by Time-Resolved Detection of Laser-Induced Transient Stress", *Appl. Opt.*, vol. 36, No. 1, pp. 402-415 (1997).

* cited by examiner

*Primary Examiner* — Michael Nghiem
*Assistant Examiner* — Felix Suarez
(74) *Attorney, Agent, or Firm* — Fitzpatrick, Cella, Harper & Scinto

(57) ABSTRACT

A measurement apparatus includes an elastic detector configured to detect an elastic wave by utilizing photoacoustic tomography and to convert the elastic wave into a detection signal, and a signal processor configured to calculate an absorption characteristic of a heterogeneous part included in a homogeneous part of a scattering medium based on $\mu_a = 2P(z)/(\Gamma\Phi(z))$ where $\mu_a$ is the absorption coefficient at distance z from the light source, $P(z)$ is the pressure of the elastic wave at distance z, $\Gamma$ is a Grüneisen coefficient, and $\Phi(z)$ is the light intensity at the position of the heterogeneous part, the signal processor obtaining the light intensity by approximating a signal component derived from the homogeneous part separated from a signal component derived from the heterogeneous part in the scattering medium by utilizing the detection signal output from the elastic wave detector.

6 Claims, 5 Drawing Sheets

MEASUREMENT APPARATUS

This application claims foreign priority benefit based on Japanese Patent Application 2008-237253, filed Sep. 17, 2008, the entire contents of which are hereby incorporated by reference herein in their entirety.

BACKGROUND OF THE INVENTION

1. Field of the Invention

The present invention relates to a measurement apparatus.

2. Description of the Related Art

Photoacoustic tomography ("PAT") is a known measurement technique of a spectroscopic (or attenuation) characteristic in biological tissue. PAT is a method that utilizes a difference in absorption of light energy as between a target region, such as a tumor (object), and background tissue (scattering medium), and receives through an elastic wave detector an elastic wave (typically an ultrasonic wave) that occurs as a result of the target region absorbing irradiated light energy and instantly expanding (U.S. Pat. No. 6,738,653).

When a stress confinement condition is met in which a pulse width of the light irradiated upon the target object from the light source is shorter than the stress relaxation time, the elastic wave has a sound pressure expressed by the following equation using a distance "z" from the light source, which is proportional to the light intensity and the absorption coefficient at a position of the target region that is a sound source. Here, P(z) is a pressure of the elastic wave at distance z, $\Gamma$ is a Grüneisen coefficient (heat-acoustic conversion efficiency), and $\mu_a(z)$ is an absorption coefficient at distance z. $\Phi(z)$ is the light intensity at distance z.

$$P(z) = \frac{1}{2}\Gamma\mu_a(z)\Phi(z) \quad \text{Equation 1}$$

In the field of diffused optical tomography ("DOT"), it is known that the light intensity $\Phi(z)$ in the scattering medium follows the following equation when absorption and scattering are viewed macroscopically. DOT is a measurement technique that introduces near-infrared light into the scattering medium and detects the diffused light. Here, "A" is a proportionality constant, and $\mu_{eff}$ is an effective attenuation coefficient.

$$\Phi(z) = A\Phi_0 \exp(-\mu_{eff} z) \quad \text{Equation 2}$$

FIG. 1 shows a sound pressure distribution of an elastic wave when there is a heterogeneous object (for example, having a higher absorption coefficient) in a scattering medium that can be considered homogeneous. An object signal region H has a bipolar-shaped waveform similar to a letter N, and a background signal region B—the region other than the object signal region H—exponentially changes (Valery V. Tuchin, *Handbook of Optical Biomedical Diagnostics*, pp. 585-646; Rinat O. Esenaliev et al., "Sensitivity of Laser Opto-Acoustic Imaging in Detection of Small Deeply Embedded Tumors," *IEEE Journal Of Selected Topics In Quantum Electronics*, Vol. 5, No. 4, pp. 981-988 (1999)). M. Xu et al., "Photoacoustic Imaging in Biomedicine," Review of Scientific Instruments 77, 041101 (2006), and A. Oraevsky et al., "Measurement of Tissue Optical Properties by Time-Resolved Detection of Laser-Induced Transient Stress," *Appl. Opt.*, Vol. 36, No. 1, pp. 402-415 (1997) propose to use Equation 2 to fit the background signal component that indicates the homogeneous part and to calculate an attenuation coefficient.

The spectroscopic (or attenuation) characteristic is affected by both the absorption (spectroscopic) characteristic and the scattering (spectroscopic) characteristic in the scattering medium. Acquisition of the absorption characteristic is desired because an amount of each of the components of the medium, such as hemoglobin, collagen, and water, can be calculated from the absorption characteristic of the light. However, in the attenuation coefficient, the absorption characteristic and the scattering characteristic are not separated and the absorption characteristic cannot be precisely evaluated. Conventional PAT cannot obtain the absorption characteristic. Moreover, unlike the proposals of Xu and Oraevsky, it is important to evaluate a characteristic of the object in addition to a calculation of the attenuation coefficient of the background signal.

SUMMARY OF THE INVENTION

The present invention provides a measurement apparatus that utilizes PAT and can more precisely measure an absorption characteristic of a scattering medium.

A measurement apparatus according to one aspect of the present invention configured to measure an absorption characteristic of a scattering medium an elastic detector configured to detect, by utilizing a photoacoustic tomography, an elastic wave that occurs as a result of light from a light source being absorbed in the scattering medium, and to convert the elastic wave into a detection signal, and a signal processor configured to calculate an absorption characteristic of a heterogeneous part included in a homogeneous part of the scattering medium based on the equation $\mu_a = 2P(z)/(\Gamma\Phi(z))$, where $\mu_a$ is the absorption coefficient at a distance z from the light source, P(z) is a pressure of the elastic wave at distance z, $\Gamma$ is a Grüneisen coefficient, and $\Phi(z)$ is the light intensity at a position of the heterogeneous part, the signal processor obtaining the light intensity by approximating a signal component derived from the homogeneous part separated from a signal component derived from the heterogeneous part in the scattering medium by utilizing the detection signal output from the elastic wave detector.

Further features of the present invention will become apparent from the following description of exemplary embodiments with reference to the attached drawings.

DESCRIPTION OF THE EMBODIMENTS

Referring now to the accompanying drawings, a description will be given of embodiments of the present invention. The elastic wave of this embodiment contains a variety of waves, such as a sound wave, an ultrasonic wave, an acoustic wave, and a photoacoustic wave, and is an elastic wave that occurs in the scattering medium as a result of that the light such as near-infrared light is irradiated upon the inside of the scattering medium.

First Embodiment

The first embodiment utilizes Equation 2 to calculate an attenuation coefficient of the background signal from a medium part (homogeneous part) in which an absorption characteristic and a scattering characteristic (which will be referred to as an "absorption-scattering characteristic" hereinafter) can be considered uniform in the scattering medium. Next, this embodiment utilizes the calculated attenuation coefficient and Equation 2 to calculate the light intensity at the position of a heterogeneous part that is an object of examination. Thereby, this embodiment can calculate the light intensity at an arbitrary position in the scattering medium, and measure the absorption coefficient (or absorption characteristic) of the object in accordance with Equation 1.

Figure 2:
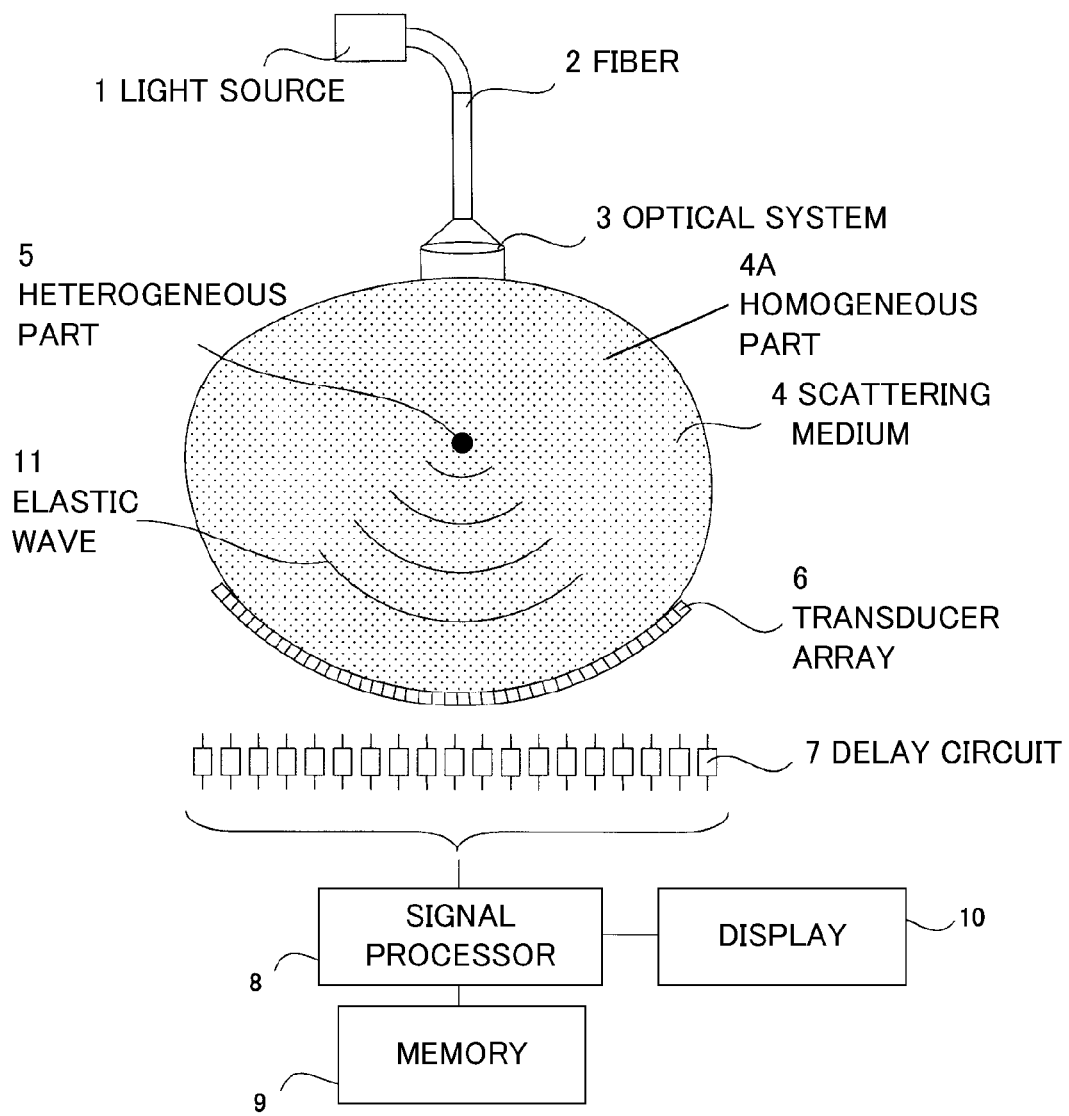
FIG. 2 is a block diagram of a measurement apparatus to which the present invention is applicable.

FIG. 2 is a block diagram of a measurement apparatus (such as an optical mammography unit) according to this embodiment. A light source 1 generates pulsed light having a wavelength in a near-infrared band, and irradiates the pulsed light into a scattering medium 4 via a fiber 2 after an optical system 3 expands the light. The light incident upon the scattering medium 4, such as biological tissue (for example, breast tissue) propagates and repeats the absorption and scattering in the scattering medium 4. The energy absorbed in the scattering medium 4 is converted into heat and induces an elastic wave 11 through the thermoelastic process. At this time, the pulse width of the light source 1 is set so that it is shorter than the stress relaxation time and satisfies the stress confinement condition.

The scattering medium 4 has a homogeneous part 4a and a heterogeneous part 5. The homogeneous part 4a is a part in which the absorption characteristic and the scattering characteristic can be considered uniform in the scattering medium. The background signal region B shown in FIG. 1 corresponds to a region of the homogeneous part 4a. On the other hand, the heterogeneous part 5 is a part of a tumor or another object in which the absorption-scattering characteristic is not uniform, and is an absorber having a higher absorption characteristic than the homogeneous part 4a in this embodiment. The object signal area H shown in FIG. 1 corresponds to a region of the heterogeneous part 5.

Figure 1:
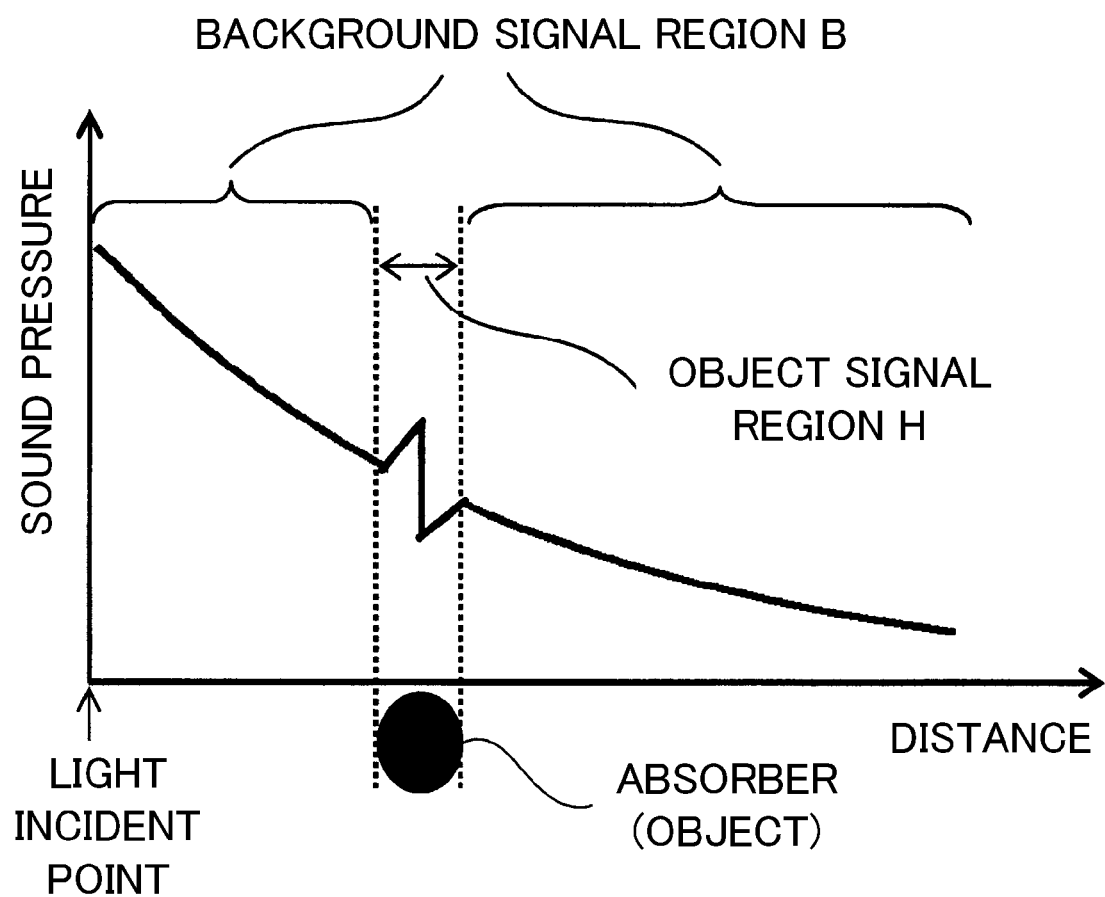
FIG. 1 is a graph showing a relationship between distance from a light source and sound pressure of an elastic wave in the PAT.
Figure 3:
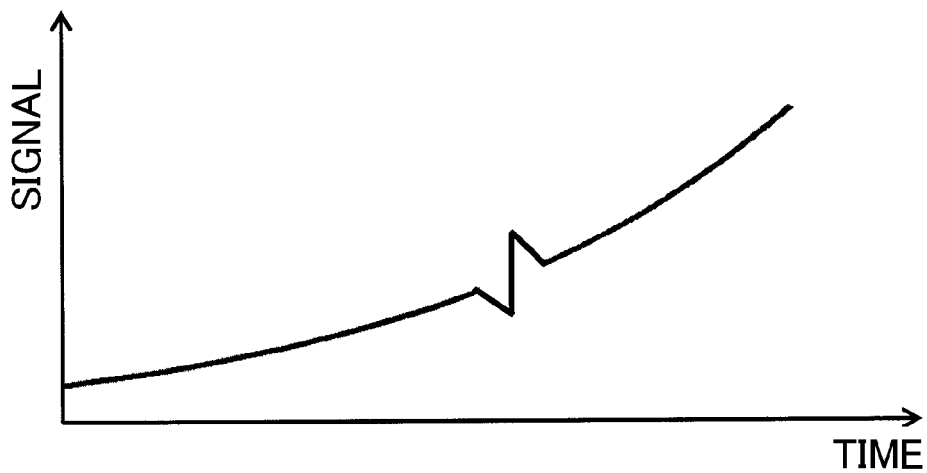
FIG. 3 is a graph showing a time response of a signal when one device in a transducer array shown in FIG. 2 detects the sound pressure distribution shown in FIG. 1 in a first embodiment.

The irradiation of the pulsed light provides the sound pressure distribution in the scattering medium 4 as shown in FIG. 1 in accordance with the Equation 1. The time response of the signal detected by one device in a transducer array 6. Thus, the transducer array 6 serves as an elastic wave detector configured to receive the elastic wave 11 that occurs as a result of the scattering medium 4 absorbing the light from the light source 1 utilizing photoacoustic tomography ("PAT") and to convert the elastic wave 11 into an electric signal. The signal shown in FIG. 3 is output from each device of the transducer array 6, and transmitted to a signal processor 8 via a delay circuit 7. The photoacoustic signals are measured by changing the light incident position and the incident wavelength arbitrarily, and is stored in a memory 9, as well as the measurement condition at the same time. After the measurement ends, the signal processor 8 starts an analysis.

Figure 4:
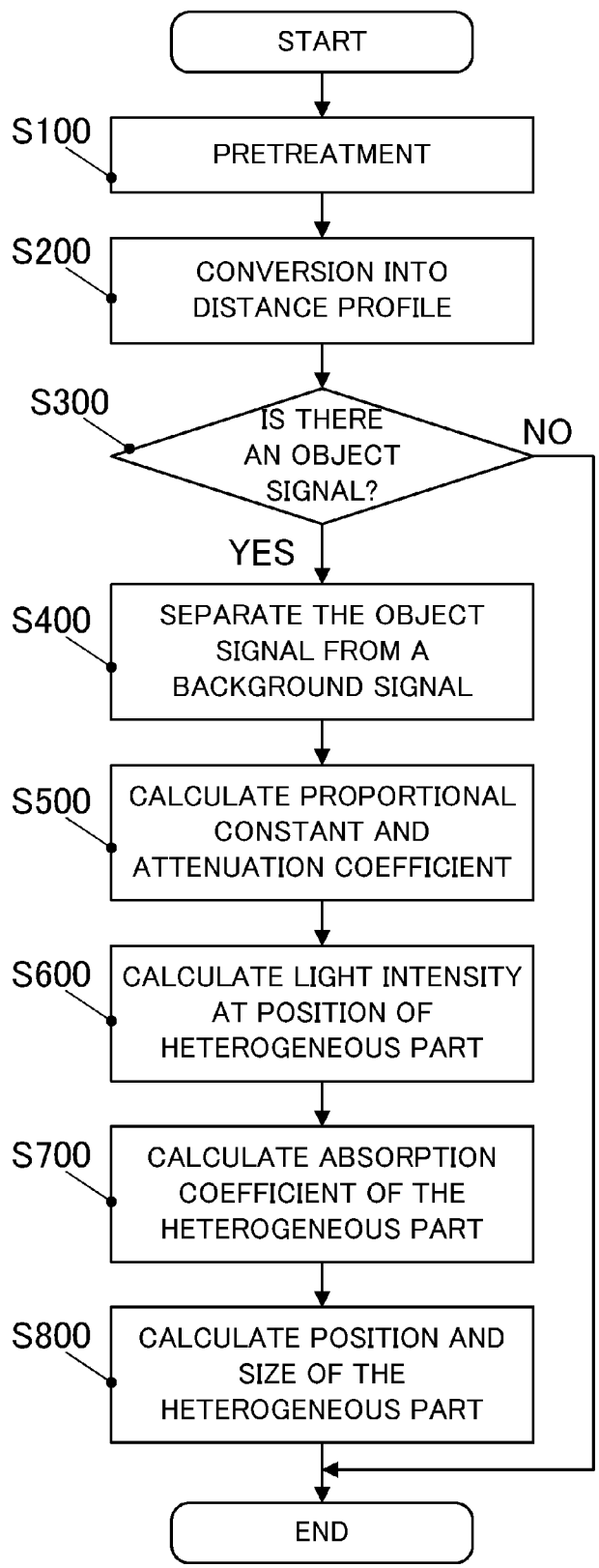
FIG. 4 is a flowchart for explaining an operation of a signal processor of the measurement apparatus shown in FIG. 2 according to a first embodiment.
Figure 7:
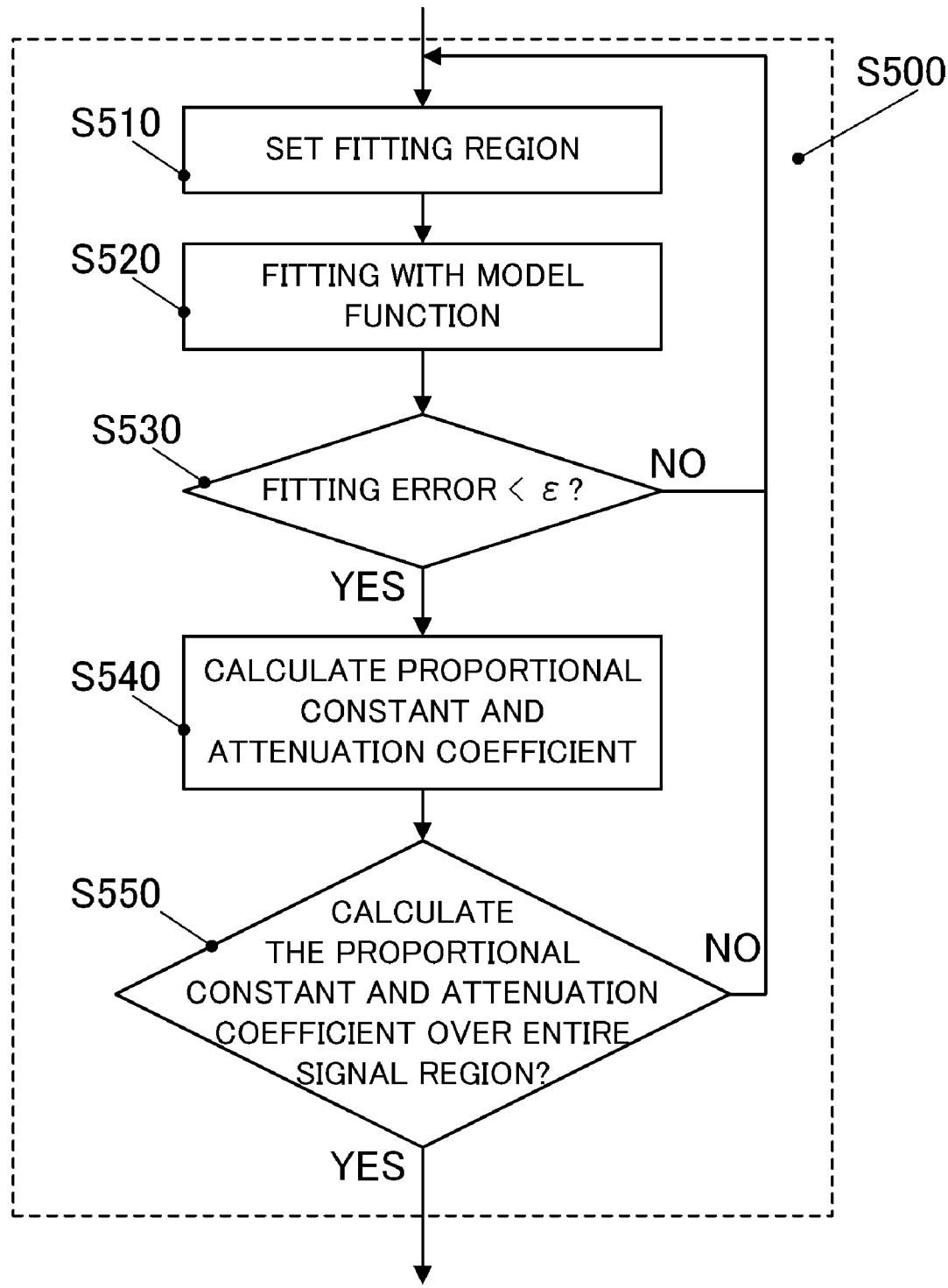
FIG. 7 is a flowchart for explaining an operation of a signal processor according to the second embodiment.

FIG. 4 shows a process flow of the signal processor 8. In FIG. 4, "S" is an abbreviation of the step, similar to FIGS. 5 and 7. Initially, the signal processor 8 performs a pretreatment for a detection signal output from each transducer (S100). In the pretreatment, the signal processor 8 removes a noise component by using filtering, such as an averaging process. Next, the signal processor 8 converts the time profile of the signal shown in FIG. 3 into a profile of the distance and the sound pressure shown in FIG. 1 (S200).

Next, the signal processor 8 determines whether there is an object signal (S300), and ends the process when determining that there is no object signal (No of S300). In this case, it is determined that the scattering medium is normal.

On the other hand, when the signal processor 8 determines that there is an object signal (Yes of S300), the signal processor 8 separates an (object) signal component of the heterogeneous part 5 in the scattering medium 4 from a (background) signal component derived from the homogeneous part 4a (S400). In other words, the signal processor 8 uses only the background signal component for S500 below, and does not use the object signal component. A determination and separation method of the object signal may compare a difference value between neighboring regions in the waveform and extracts the difference value whose change rate is equal to or higher than a threshold, or may separate or filter a component equal to or higher than a threshold frequency through the frequency analysis. When the waveform has an N shape, the signal component may be separated by checking an inflection point. Data of a continuous background signal component is generated by removing the object signal component, and linearly interpolating discontinuous points in the background signal component or interpolating the background signal component with a spline. At this time, the object signal region H and the distance "z" from the light incident point are calculated and stored in the memory 9.

Next, the signal processor 8 fits (approximates) the background signal component with the function shown in the Equation 2, and obtains a proportional constant "A" and an attenuation coefficient $\mu_{eff}$ in the region that can be regarded as a homogeneous medium of the scattering medium 4 (S500). Thus, fitting corresponds to the proportional constant "A" and the attenuation coefficient $\mu_{eff}$ of Equation 2.

Next, the signal processor 8 reads out the distance "z" from the light incident point to the object signal from the memory 9, and calculates the light intensity at the (object) position of the heterogeneous part contained in the homogeneous part 4a using the calculated function fitted in S500 (S600). Next, the signal processor 8 reads out the sound pressure amplitude of the object signal from the memory 9, and calculates the absorption coefficient $\mu_a$ of the heterogeneous part 5 utilizing Equation 1 (S700). In this case, Equation 1 is turned into the following equation and the light intensity and the sound pressure are substituted. As described above, P(z) is the pressure of the elastic wave at distance z, $\Gamma$ is a Grüneisen coefficient (heat-acoustic conversion efficiency), $\mu_a(z)$ is the absorption coefficient at distance z, and $\Phi(z)$ is the light intensity at distance z.

$$\mu_a = \frac{2P(z)}{\Gamma \Phi(z)} \qquad \text{Equation 3}$$

The present invention in this aspect is notable for properly removing an object signal from a signal of a sound pressure profile, and in fitting the background signal that is obtained by interpolating the discontinuing part in accordance with Equation 2. By setting a fitting region with Equation 2 to the background signal other than the object signal, the attenuation characteristic (proportionality constant A and the attenuation coefficient $\mu_{eff}$) in the scattering medium can be obtained more precisely. Therefore, the precision of the absorption coefficient $\mu_a$ calculated by Equation 3 can be improved.

After the process from S100 to S700 is performed for the entire transducer array 6, the signal processor 8 calculates the position of the object in the scattering medium 4 from the transmission time of the elastic wave 11 and the size of the object from the bipolar waveform (S800).

The process from S100 to S800 is similarly performed for various measurement data obtained by changing the light incident position, and the three-dimensional distribution of the heterogeneous part 5 in the scattering medium 4 can be reconstructed from the obtained information.

According to this embodiment, the signal processor 8 can precisely calculate the absorption coefficient of the absorbing medium since the signal processor 8 estimates the light intensity in the scattering medium 4 in S600. In addition, the signal processor 8 calculates the absorption coefficient $\mu_a$ for each of a plurality of wavelengths, and calculates ratios of major ingredients of the scattering medium 4, such as oxygenated hemoglobin, deoxygenated hemoglobin, water, fat, and collagen, from the spectroscopic information. A display 10 may display an object distribution for a certain wavelength, or may display the internal distribution of the component ratio.

While fitting of S500 uses the Equation 2, the following equation in accordance with the light diffusion theory may be used to estimate the attenuation of the light intensity and to infer $\mu_a$ depending upon the light incident condition upon the scattering medium 4.

$$\Phi(z) = A\Phi_0 \frac{\exp(-\mu_{eff} z)}{z} \quad \text{Equation 4}$$

The elastic wave detector of this embodiment may be a single plate or curved transducer rather than the transducer array 6 or may be a detection system including an acoustic lens. In addition, the attenuation coefficient $\mu_{eff}$ may be treated approximately equivalent with the absorption characteristic for a medium having a uniform scattering characteristic, and the attenuation coefficient $\mu_{eff}$ may be three-dimensionally reconstructed and displayed.

Second Embodiment

Figure 5:
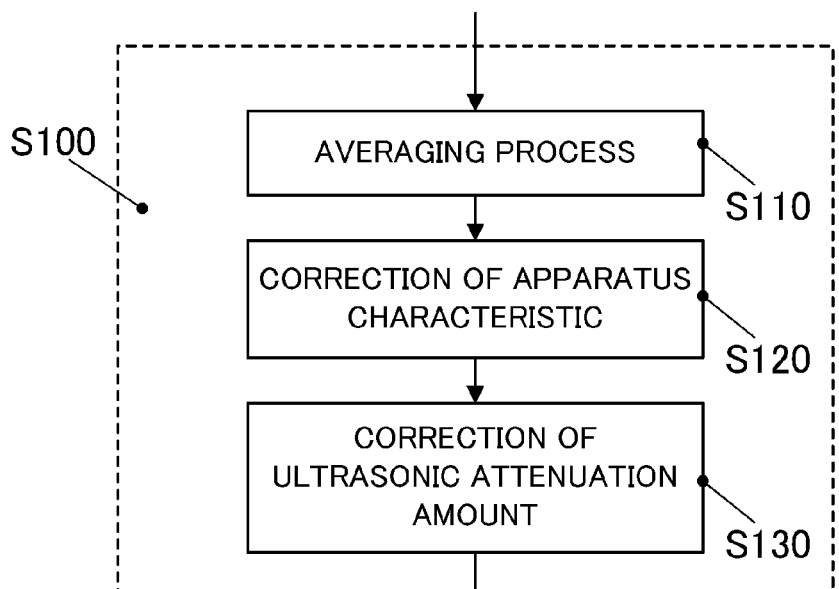
FIG. 5 is a flowchart for explaining an operation of a signal processor according to a second embodiment.

A second embodiment uses the measurement apparatus shown in FIG. 2, basically utilizes the flow shown in FIG. 4, but differs from the first embodiment in S100, S500, or S600. FIG. 5 shows a flow showing details of the pretreatment of this embodiment (S100 shown in FIG. 4).

Initially, similar to the first embodiment, the signal processor 8 filters a noise signal through an averaging process (S110). The memory 9 previously stores an apparatus characteristic, such as a resonance frequency for each device of the transducer 6 and output fluctuation including an amplifier. Before the measurement, the apparatus characteristic that fluctuates in accordance with the measurement environment is provisionally measured and a correction value is calculated and stored in the memory 9.

Next, the signal processor 8 corrects the apparatus characteristic for each channel of the transducer array 6 for the obtained signal waveform (S120). For example, the correction, such as correcting the resonance frequency of the transducer in the frequency space, or adjusting the output fluctuation.

Next, the signal processor 8 corrects the attenuation when the elastic wave 11 propagates in the scattering medium 4.

Thus, the signal processor 8 corrects an attenuation amount in accordance with the distance from the light source of each detection signal before approximation or fitting (S130). In the scattering medium, such as an biological tissue, the attenuation of the elastic wave is mainly caused by the absorption and the influence of scattering is almost negligible. For example, assume the absorption coefficient $\alpha$ of a sound wave in the biological tissue is expressed as follows, and the attenuation effect by this absorption coefficient $\alpha$ is weighed similar to the attenuation of the light intensity and the attenuation amount is estimated and corrected. Here, "a" is a constant $[\text{cm}^{-1} \text{MHz}^{-b}]$.

$$\alpha = af^b \quad \text{Equation 5}$$

Figure 6:
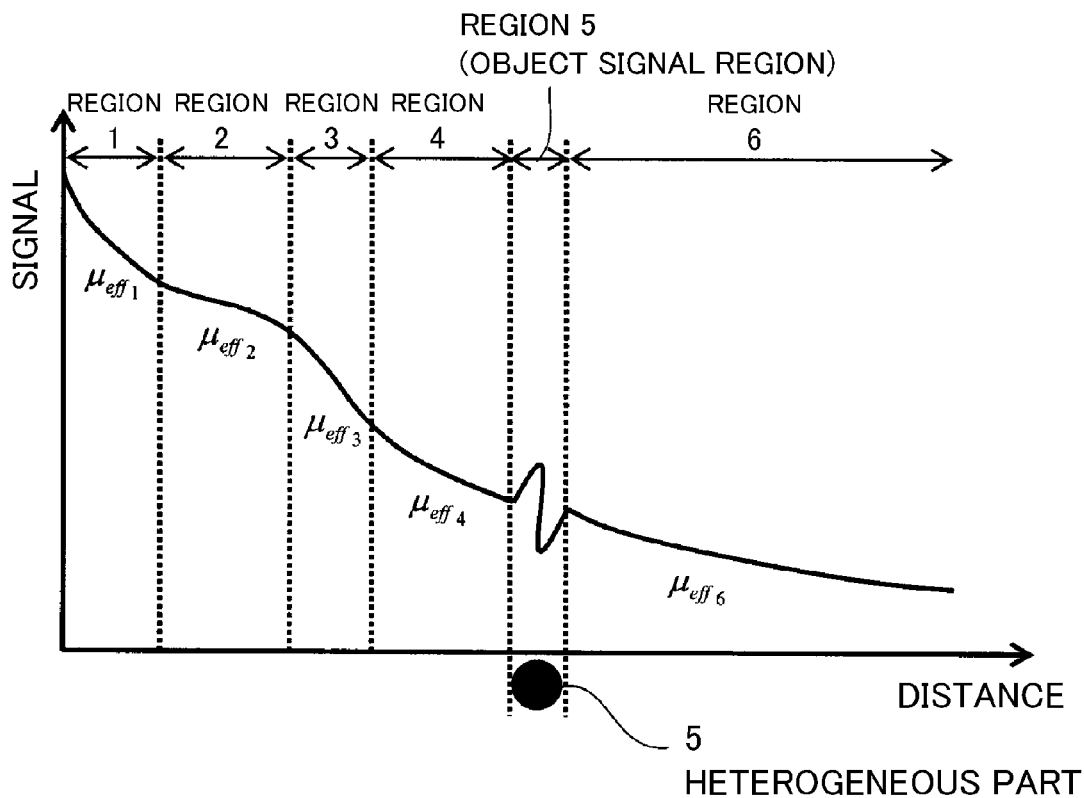
FIG. 6 is a graph showing a time response of a signal when one device of a transducer array shown in FIG. 2 detects the sound pressure distribution shown in FIG. 1 in the second embodiment.

This embodiment assumes that there is the heterogeneous part 5 in a plurality of media that can be considered homogeneous. The homogeneous medium provides the sound pressure profile which is characterized with the proportionality constant "A" and the attenuation coefficient $\mu_{eff}$. The signal shown in FIG. 6 is detected by adding the signals of a plurality of homogeneous media (S200). The flow shown in FIG. 4 is applicable to a calculation of the absorption coefficient of the heterogeneous part 5, but S500 is replaced with the process shown in FIG. 7. Similar to the first embodiment, this process is performed for the background signal component from which the object signal component has been separated.

Initially, the signal processor 8 specifies a region in the signal waveform that is to receive the fitting for calculating the absorption coefficient or determines the fitting region (S510). Here, the fitting region indicates a distance range in the abscissa axis shown in FIG. 6. For example, initially, the entire signal waveform is targeted.

Next, the signal processor 8 fits the signal waveform using the function of Equation 2 or 4 (S520), and determines whether the fitting error is smaller than a preset permissible error $\epsilon$ (S530). When the signal processor 8 determines that the fitting error falls within the permissible error $\epsilon$ (Yes of S530), the attenuation coefficient obtained by the fitting is set to the attenuation coefficient of the region set by S510 (S540). Thereafter, the signal processor 8 determines whether the attenuation coefficient is calculated in the entire signal region (S550). The permissible value $\epsilon$ of the fitting error is determined so that it will not be excessively sensitive to high-frequency noise and so that it can properly express the background signal. The permissible error $\epsilon$ can be arbitrarily set by the scattering medium to be measured.

When the signal processor 8 determines that the fitting error is equal to or higher than a permissible error $\epsilon$ (No of S530), the flow returns to S510 and the signal processor 8 sets the fitting area again. In this case, the distance range of the fitting region is narrowed so that the fitting can fall within the permissible error $\epsilon$, and the signal processor 8 repeats the flow from S510 to S530. By limiting the filling region, the attenuation coefficient in which the fitting error falls within the permissible error $\epsilon$ is calculated in the region 1 shown in FIG. 6, for example. Since the signal processor 8 calculates the attenuation coefficient so that the fitting error falls within the permissible error $\epsilon$, the flow again returns to S510 and the signal processor 8 executes the above process when the signal processor 8 determines that it has not yet calculated the attenuation coefficients for all the signal regions (No of S550). At this time, the fitting process is resumed from the region 2 for which the attenuation coefficient has not yet been calculated.

Thus, the signal processor 8 performs the process from S510 to S550, and thereby calculates the absorption coefficient for each region that can be regarded as a homogeneous medium, as shown in FIG. 6. In FIG. 6, regions 1-4 and 6 correspond to the background signal region, and region 5 corresponds to the object signal region. In FIG. 6, there are five homogeneous parts 4a, and a plurality of homogeneous parts 4a have different attenuation coefficients and proportional constants. In calculating the light intensity at the object position after the attenuation coefficient is thus calculated for each of the plurality of regions (S600), the signal processor 8 estimates the light attenuation at each region from the light incident point to the object position as in the Equation 6, and multiplies it with the incident light intensity (S600).

$$\Phi(z) = \Phi_0 \prod_j A_j \exp\left[-\mu_{\mathit{eff}_j}(z_j - z_{j-1})\right] \quad \text{Equation 6}$$

When the light intensity is calculated at the object position in accordance with Equation 6, the signal processor 8 then utilizes $\mu_a = 2P(z)/(\Gamma\Phi(z))$ of Equation 3 and calculates the absorption coefficient of the heterogeneous part 5, similar to the first embodiment. The process of this embodiment enables the light intensity of the object position to be precisely calculated by dividing the heterogeneous medium into regions that can be regarded as homogeneous media and by calculating the attenuation coefficient for each region, and the absorption coefficient of the object to be precisely calculated. This embodiment is characterized in the process from S500 to S600.

This embodiment also measures the absorption spectroscopic information with a plurality of wavelengths, and can calculate the ratios of the major components of the scattering medium 4. In addition, while this embodiment uses the function indicated by Equation 2 or 4, the attenuation of the light intensity may be estimated in accordance with another function predicted from the light diffusion theory depending upon the apparatus condition, and the attenuation coefficient $\mu_{\mathit{eff}}$ may be inferred.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A measurement apparatus configured to measure an absorption characteristic of a scattering medium, said measurement apparatus comprising:
    an elastic detector configured to detect an elastic wave that occurs as a result of light from a light source being absorbed in the scattering medium, and to convert the elastic wave into a detection signal; and
    a signal processor configured to separate, from the detection signal, a background signal component derived from a homogeneous part in the scattering medium and an object signal component derived from a heterogeneous part in the scattering medium,
        to obtain an attenuation coefficient of the scattering medium by utilizing the background signal component,
        to obtain a light intensity at a position of the heterogeneous part by utilizing the attenuation coefficient, and
        to obtain an absorption coefficient of the heterogeneous part by utilizing the light intensity and a pressure amplitude of the object signal component.

2. The measurement apparatus according to claim 1, wherein said signal processor corrects for attenuation when the elastic wave propagates in the scattering medium before said signal processor approximates the background signal component derived from the homogeneous part.

3. The measurement apparatus according to claim 1, wherein said signal processor divides the object signal component into a plurality of regions so that an approximation of each signal component can fall within a permissible error, and calculates an attenuation coefficient, the signal processor calculating the light intensity of the heterogeneous part by a product of attenuation coefficients of the plurality of regions.

4. The measurement apparatus according to claim 1, wherein said signal processor is configured to obtain a proportionality constant by utilizing the background signal component, and to obtain the light intensity at the position of the heterogeneous part by utilizing the attenuation coefficient and proportionality constant.

5. The measurement apparatus according to claim 1, wherein the signal processor is configured to calculate the absorption characteristic of the heterogeneous part included in the homogeneous part of the scattering medium based on $\mu_a = 2P(z)/(\Gamma\Phi(z))$ where $\mu_a$ is the absorption coefficient having a distance z from a surface of the scattering medium, P(z) is a pressure of the elastic wave having the distance z, $\Gamma$ is a Grüneisen coefficient, and $\Phi(z)$ is the light intensity at the position of the heterogeneous part.

6. The measurement apparatus according to claim 1, further comprising the light source configured to generate light.

* * * * *